United States Patent [19]
Gatten et al.

[11] Patent Number: 5,290,340
[45] Date of Patent: Mar. 1, 1994

[54] METHODS AND APPARATUS FOR DEGASSING A LIQUID

[75] Inventors: Ronald A. Gatten, Pleasanton; Leslie A. Miller, Milpitas; Thomas J. McCall, Jr., Fremont; Vance J. Nau, Cupertino, all of Calif.

[73] Assignee: Thermo Separation Products (California) Inc., Fremont, Calif.

[21] Appl. No.: 990,656

[22] Filed: Dec. 14, 1992

Related U.S. Application Data

[63] Continuation-in-part of Ser. No. 622,999, Dec. 4, 1990, Pat. No. 5,183,486.

[51] Int. Cl.$^5$ .................... B01D 19/00; B01D 15/08
[52] U.S. Cl. .......................................... 95/46; 95/259; 96/6; 96/155; 210/656; 210/198.2
[58] Field of Search ................ 55/16, 36, 55, 159, 55/189–191; 210/188, 198.2, 656

[56] References Cited

U.S. PATENT DOCUMENTS

| | | | |
|---|---|---|---|
| 3,377,778 | 4/1968 | Gaertner | 55/189 X |
| 4,079,009 | 3/1978 | Seiler et al. | 55/386 X |
| 4,271,697 | 6/1981 | Mowery, Jr. | 73/61.1 C |
| 4,293,418 | 10/1981 | Fuji et al. | 55/158 X |
| 4,325,715 | 4/1982 | Bowman et al. | 55/159 X |
| 4,371,385 | 2/1983 | Johnson | 55/190 |
| 4,374,656 | 2/1983 | Schrenker et al. | 55/170 |
| 4,430,098 | 2/1984 | Bowman et al. | 55/191 |
| 4,448,684 | 5/1984 | Paradis | 210/198.2 |
| 4,461,328 | 7/1984 | Kenney | 55/159 X |
| 4,469,495 | 9/1984 | Hiraiziumi et al. | 55/189 |
| 4,475,821 | 10/1984 | Koch et al. | 210/198.2 X |
| 4,505,149 | 3/1985 | Trumbore | 73/53 |
| 4,541,452 | 9/1985 | Paradis | 210/198.2 X |
| 4,629,561 | 12/1986 | Shirato et al. | 55/386 X |
| 4,651,087 | 3/1987 | Shirado et al. | 324/71.4 |
| 4,652,364 | 3/1987 | Shirato et al. | 210/188 X |
| 4,728,344 | 3/1988 | Stacy | 55/67 |
| 4,729,773 | 3/1988 | Shirato et al. | 55/158 |
| 4,794,954 | 1/1989 | Tokuda et al. | 138/30 |
| 4,819,478 | 4/1989 | Melcher | 210/635 X |
| 4,917,776 | 4/1990 | Taylor | 55/159 X |
| 4,952,126 | 8/1990 | Hanaoka et al. | 210/198.2 X |
| 4,981,597 | 1/1991 | Allington et al. | 210/198.2 X |
| 4,986,837 | 1/1991 | Shibata | 55/190 |
| 4,988,447 | 1/1991 | Hellinger | 210/659 |
| 5,053,060 | 10/1991 | Kopf-Sill et al. | 55/16 |
| 5,112,492 | 5/1992 | Ransohoff | 210/188 X |
| 5,183,486 | 2/1993 | Gatten et al. | 55/158 X |

FOREIGN PATENT DOCUMENTS

| | | |
|---|---|---|
| 0360604 | 3/1990 | European Pat. Off. |
| 60-257810 | 12/1985 | Japan. |
| 2-122260 | 5/1990 | Japan. |
| 2097281 | 11/1982 | United Kingdom. |

OTHER PUBLICATIONS

Bakalzar, "The Role of Dissolved Gases in High Performance Liquid Chromatography," J. Chromatography, vol. 158, pp. 277–293 (1978).

Shodex Op. Manual No. 781 for Shodex Degas-KT Series Degassing Device (undated).

*Primary Examiner*—Robert Spitzer
*Attorney, Agent, or Firm*—Killworth, Gottman, Hagan & Schaeff

[57] ABSTRACT

A degassing system is provided and includes a module for conditioning a liquid to be analyzed. The module includes a container holding a liquid, a degassing chamber, and a holder for the liquid container mounted on top of the degassing chamber. The holder provides stability to the module and contains any liquid spills. In another embodiment, the system includes an autosampler in conjunction with a degassing unit which includes a degassing chamber, a vacuum pump, and tubing for conducting liquid through the degassing chamber, which tubing is permeable to gases in the liquid.

9 Claims, 10 Drawing Sheets

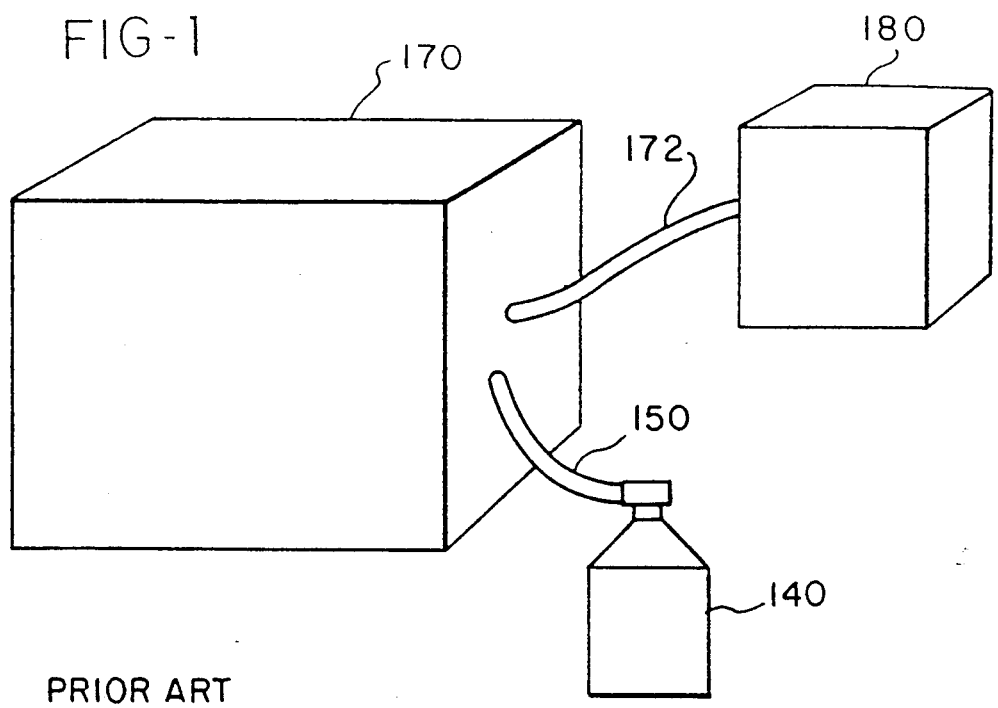
FIG-1
PRIOR ART
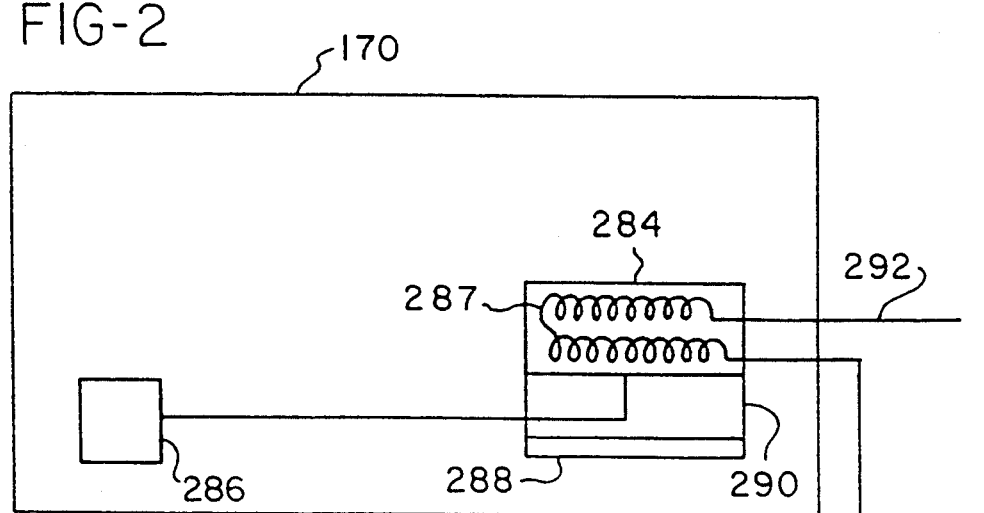
FIG-2
PRIOR ART
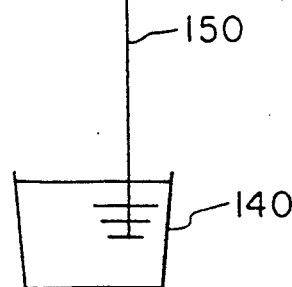

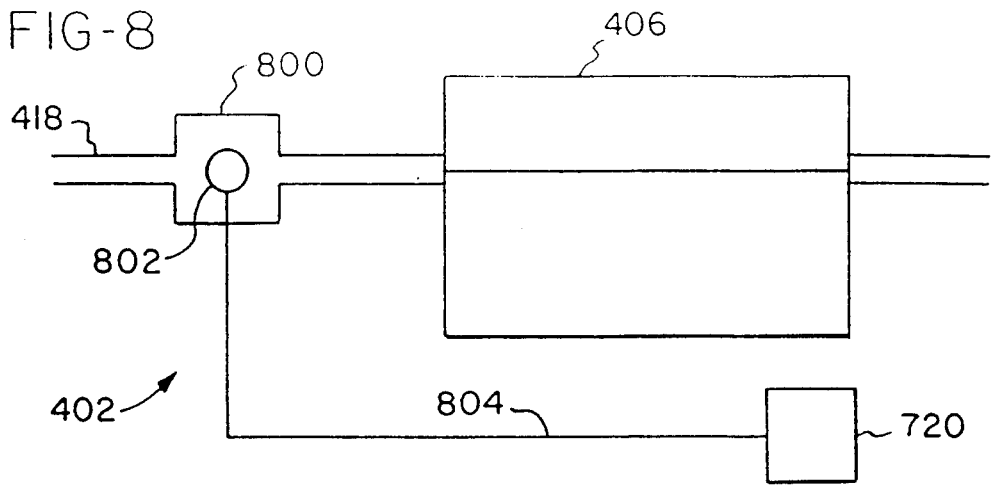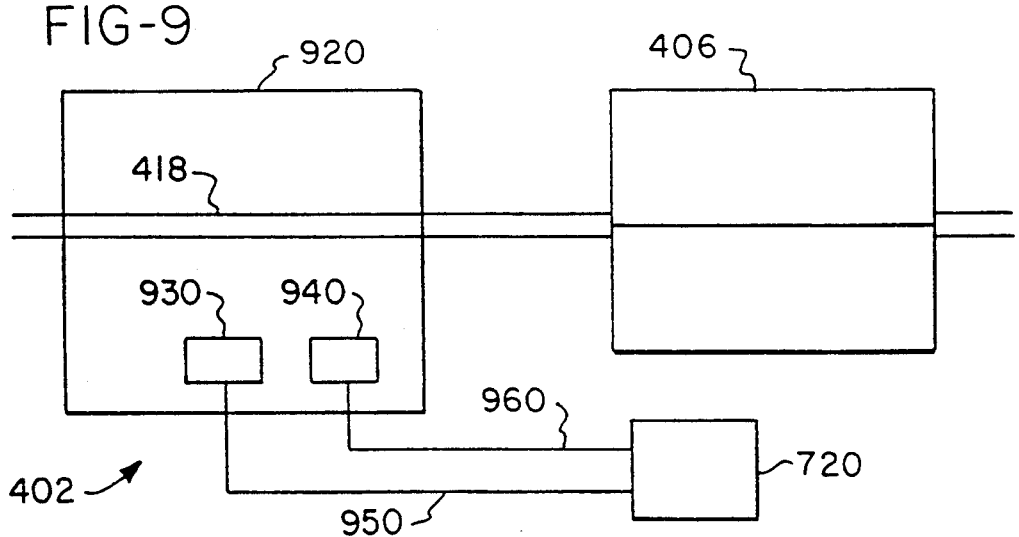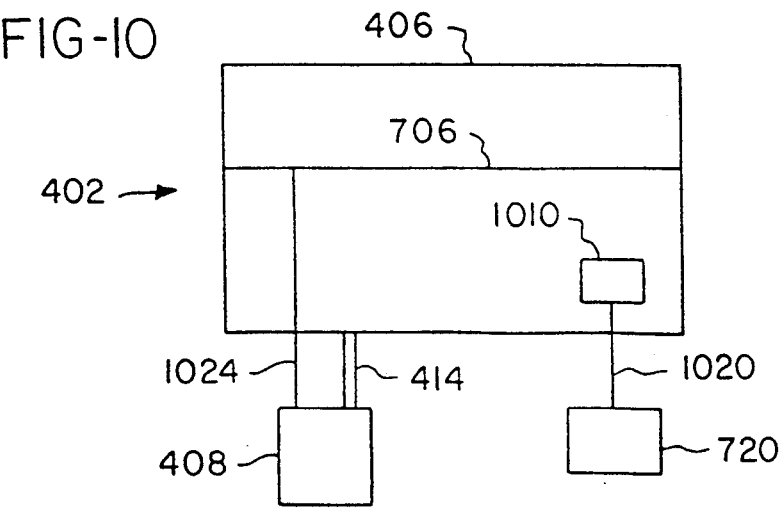

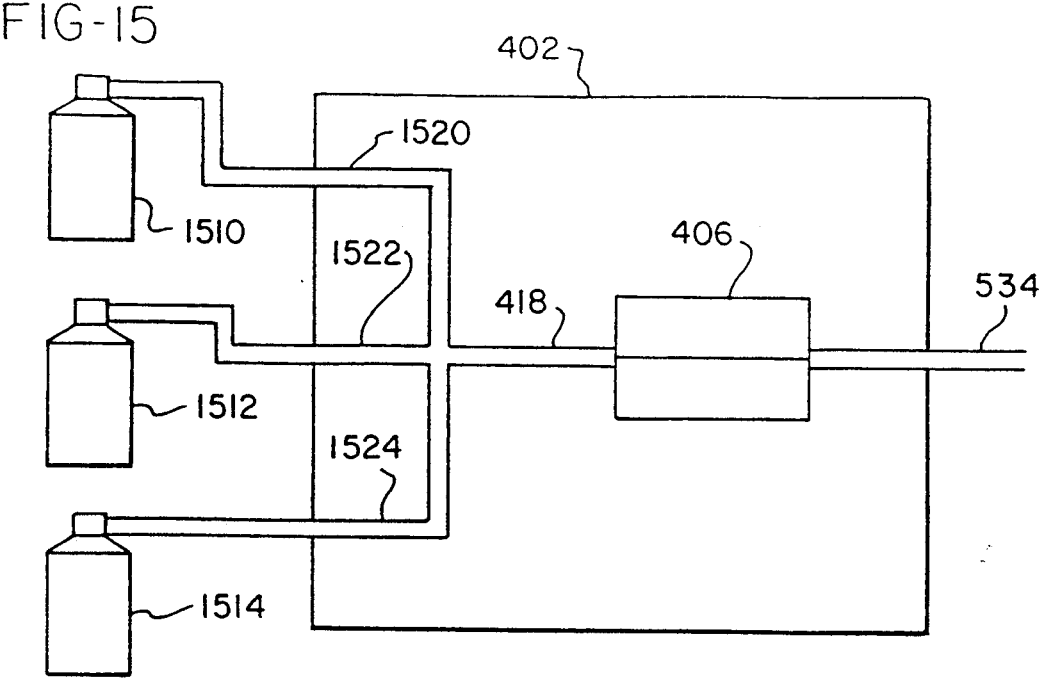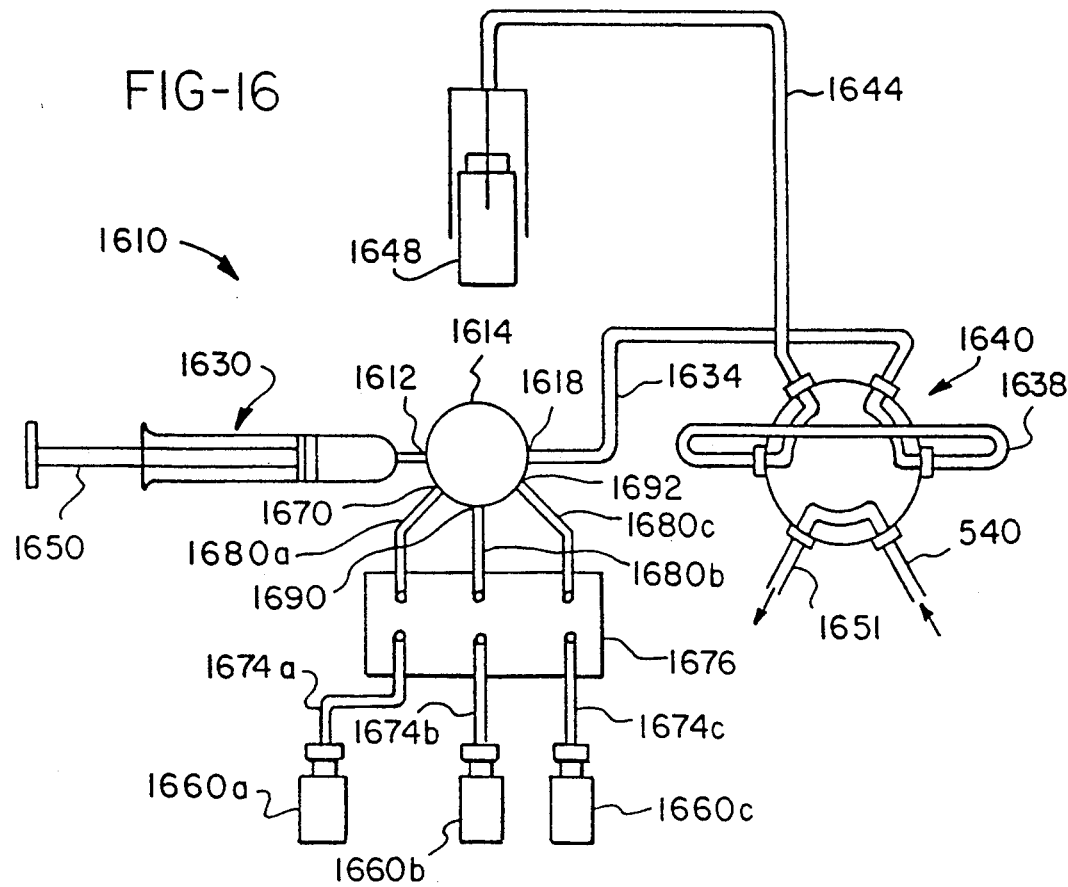

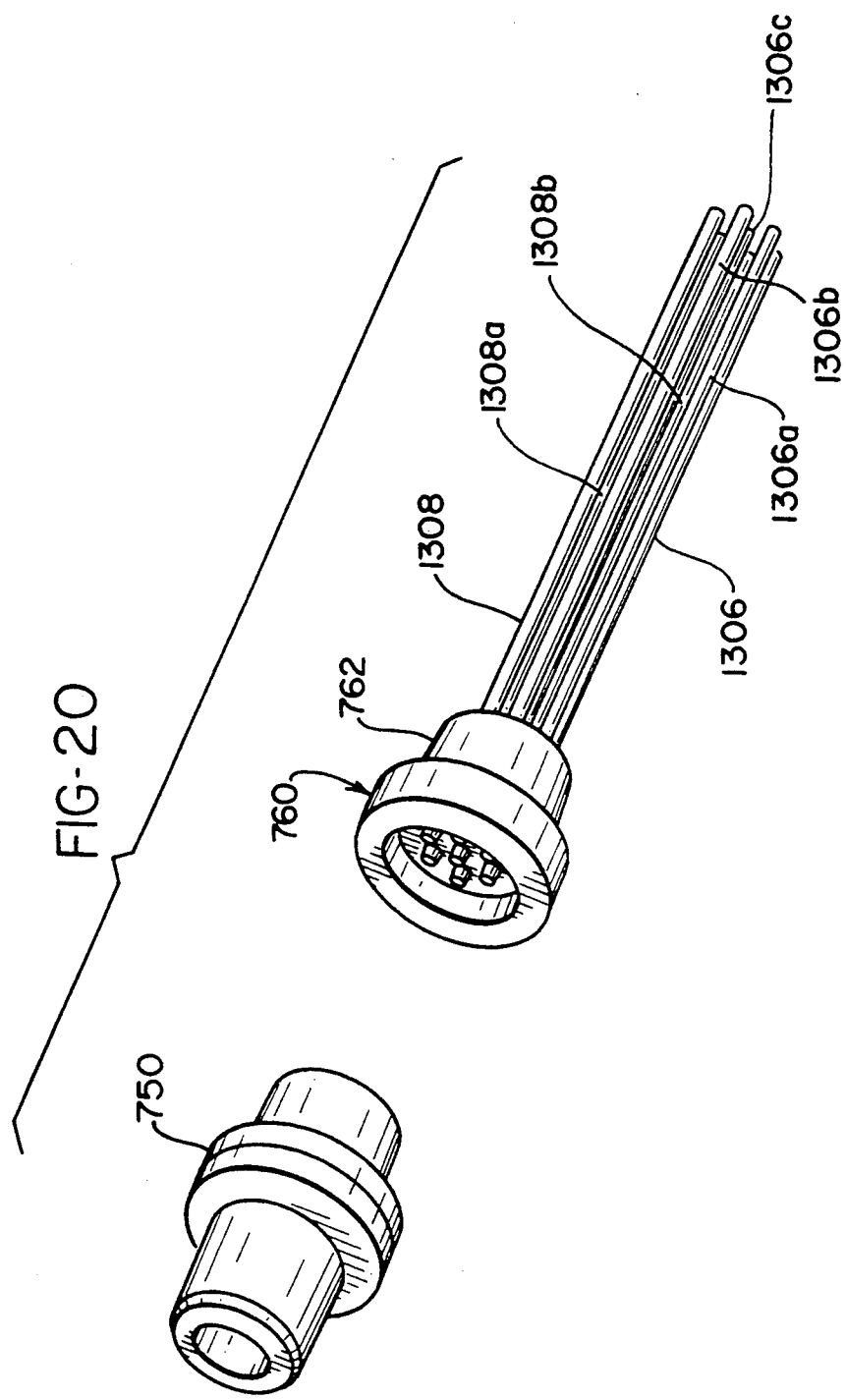

METHODS AND APPARATUS FOR DEGASSING A LIQUID

CROSS-REFERENCE TO RELATED APPLICATIONS

This is a continuation-in-part of application Ser. No. 07/622,999, filed Dec. 4, 1990, now U.S. Pat. No. 5,183,486, issued Feb. 2, 1993, the disclosure of which is hereby incorporated by reference. This application is also related to U.S. application Ser. No. 07/990,274, filed Dec. 14, 1992, and entitled METHODS AND APPARATUS FOR DEGASSING A LIQUID.

BACKGROUND OF THE INVENTION

The present invention relates to degassing a liquid, and more particularly to vacuum degassing a liquid.

Degassing is practiced in liquid chromatography to extract air from mobile phase solvents since the pressure of air (particularly oxygen) interferes with chromatographic analysis. See Bakalyar, Bradley and Honganen, *The Role of Dissolved Gases in High-Performance Liquid Chromatography*, Journal of Chromatography, 158 (1978) 277-293. In prior art systems, as shown in FIG. 1, solvent is conducted from a bottle 140 via tubing 150 to a degasser 170 where the solvent is degassed. The degassed solvent is conducted from the degasser 170 via tubing 172 to a liquid chromatography analytical system (LC analytical system) 180 for use as a mobile phase.

FIG. 2 shows a schematic diagram of a Shodex DEGAS KT-Series Degasser 170 available from Shodex Group of Tokyo, Japan. To degas the solvent, degasser 170 includes a vacuum chamber 284 and a vacuum pump 286 to create a vacuum therein. The solvent is pumped by a liquid chromatography pump (which pump is not shown in FIG. 2) from bottle 140 via tubing 150 to the vacuum chamber 284. In the vacuum chamber 284, the solvent flows through tubing 287. As the solvent flows therethrough, gas dissolved in the solvent goes out through the wall of tubing 287, which is made of a special macromolecular film, and the solvent is thus degassed. A heater 288 under a vacuum chamber base 290 can be used to heat the solvent in vacuum chamber 284 which increases the effectiveness of degassing. The degassed solvent is further pumped from vacuum chamber 284 to a LC analytical system (not shown in FIG. 2) via tubing 292. See *Shodex Operation Manual No. 781 for Shodex DEGAS KT-Series Degassing Device* available from SHOWA DENKO K.K., Specialty Chemicals Division, Shodex (Separation & HPLC) Group, 13-9, Shiba Daimon 1-Chome, Minato-ku, Tokyo 105, Japan.1110

Shodex degasser 170 of FIG. 2 can be used to degas components of a mixed solvent as is schematically shown in FIG. 3. Each of bottles 300, 302 and 304 contains a component of the solvent. The components are conducted via respective tubings 308, 310 and 312 through degasser 170 wherein each component is degassed as it passes through. Thereafter, in a portion 316 of tubing, the degassed components are mixed into a solvent which is conducted to a liquid chromatography analytical system (not shown in FIG. 3) via tubing 318.

It is desirable to provide effective methods and apparatus for degassing a liquid.

SUMMARY OF THE INVENTION

The present invention provides methods and apparatuses for effective degassing of a liquid. The invention also provides methods and apparatuses for temperature control of a liquid which is degassed, and effective arrangements of containers having the liquid, or components thereof, which are degassed. The invention can be used for preparing a mobile phase for liquid chromatography, and for preparing a sample for analysis by liquid chromatography or by other methods. Methods for testing the apparatus of the invention are also provided.

A module for conditioning a liquid is provided which comprises means for degassing the liquid, and a holder for a container having liquid. The holder is preferably mounted on top of the degassing means. Such an arrangement increases the physical stability of the container, particularly when the module is used to degas a mobile phase.

Further, a pump is provided for pumping a liquid from a container. The pump calculates the amount of liquid which is pumped, and the amount of liquid remaining in the container. The amount of liquid remaining is displayed.

Within the module, a vacuum degassing unit, for degassing a liquid is provided comprising means for conducting the liquid through a vacuum chamber and a radiator for radiating electromagnetic energy to be transmitted to the conducting means. In some embodiments, the radiator is adapted to heat the liquid or the conducting means by electromagnetic energy. Such a radiator is more efficient for heating than a conventional heat-radiating heater because the vacuum in the vacuum chamber, which is not a good conductor of heat, does not effect the radiation of electromagnetic energy. Heating with such energy enhances degassing.

In addition, several variants of the vacuum degassing unit are further provided. In one variation, a vacuum degassing unit for degassing a liquid is provided in which a heater heats the liquid before the liquid enters a vacuum chamber.

A vacuum degassing unit for degassing a liquid is also provided in which the liquid is in a state of agitation in a vacuum chamber. In some embodiments, when the vacuum chamber is at vacuum, gas is extracted from the portions of the liquid adjacent to the walls of the tubing for conducting the liquid. The liquid is agitated so as to bring other portions of the liquid close to the walls of the tubing. Effectiveness of degassing is increased thereby.

To further enhance degassing, a vacuum degassing unit for degassing a liquid is provided in which the liquid is conducted through a vacuum chamber via a tube. The tube is wound in coils around a bobbin. The adjacent coils of the tube are spaced from each other. In some embodiments, such a construction increases the tubing surface area exposed to vacuum in the vacuum chamber and thus makes degassing more efficient.

In a further aspect of the invention, a vacuum degassing unit for degassing a solvent for use in a liquid chromatography analytical system is provided which comprises a vacuum chamber, a pump for creating a vacuum in the chamber, and a means for stopping the pump or for restricting the pump operation for a duration of a chromatographic run. It is desirable in some applications to stop the vacuum pump for a duration of the run so as not to change the oxygen level in the solvent during the run.

As well, in this further aspect of the invention, an apparatus for degassing a solvent is provided comprising a vacuum chamber, a first pump (vacuum pump) for creating a vacuum in the chamber, and a second pump (liquid pump) for pumping the solvent through the chamber. The first and the second pumps are controlled in response to chromatographic conditions in the LC analytical system so as to optimize the conditions. In one embodiment, the second pump is controlled so as to adjust the flow rate of the solvent through the vacuum chamber so as to optimize the chromatographic conditions.

In a still further aspect of the present invention, an autosampler is provided comprising means for injecting a sample into a mobile phase, a vacuum degassing unit for degassing a solvent, and means for conducting the degassed solvent through the injecting means. In one embodiment, the solvent is a flush solvent used to flush the injecting means. In another embodiment, the solvent is a diluent or a reagent used for sample dilution or chemical transformation.

Further, an autosampler is provided comprising means for connecting a sample container to a vacuum degassing unit and means for connecting the vacuum degassing unit to an injector valve. In one embodiment, the autosampler is used to degas a sample to be analyzed by liquid chromatography.

A liquid chromatography analytical system for analyzing a sample is provided comprising a vacuum chamber for extracting a gas from the sample. The extracted gas is used for producing chromatographic information.

In accordance with the present invention, various methods are provided for using and testing the apparatuses disclosed herein. In particular, a method is provided for providing a mixed mobile phase. The components of the mobile phase are mixed, the mixed mobile phase is placed into a vacuum chamber, degassed, and conducted to a LC analytical system. Mixing the components of the mobile phase before degassing the mobile phase is advantageous when the solubility of gases in the mixed mobile phase is lower than the solubility of the gases in the components.

A method is also provided for testing the conduit (such as tubing or a membrane) which conducts a liquid to be degassed through the vacuum chamber. Namely, a selected gas is introduced into the conduit. A predetermined level of vacuum is reached in the chamber. As the vacuum level decays, the time of decay is measured. The condition of the conduit is determined from the time of decay. For example, when the walls of the tubing become contaminated by particles suspended in the liquid, the time of decay is longer. The contaminated condition of the tubing walls is determined from the increased time of decay.

A method is provided for using a vacuum chamber for the "reverse" purpose of dissolving a gas in the mobile phase. It is sometimes advantageous to dissolve some gas in the mobile phase. The gas is put into the vacuum chamber under pressure so as to dissolve at least a portion of the gas in the mobile phase. The mobile phase is conducted to the analytical system.

Other aspects and objects of the invention will become apparent from the following description, the drawings, and the appended claims.

BRIEF DESCRIPTION OF THE DRAWINGS

FIG. 1 shows a block diagram of a prior art system including a degasser and a liquid chromatography analytical system.

FIG. 2 shows a schematic diagram of a prior art degasser.

FIG. 8 shows a schematic diagram of a portion of another vacuum degassing unit according to this invention.

FIG. 9 shows a schematic diagram of a portion of another vacuum degassing unit according to this invention.

FIG. 10 show a schematic diagram of another vacuum degassing unit according to this invention.

FIG. 15 shows a schematic diagram of a vacuum degassing unit of this invention used to degas a mixed mobile phase.

FIG. 16 shows a schematic diagram of an autosampler according to this invention.

FIG. 20 shows a schematic view of the multiple tube plug according to the present invention.

DESCRIPTION OF THE PREFERRED EMBODIMENTS

Figure 3:
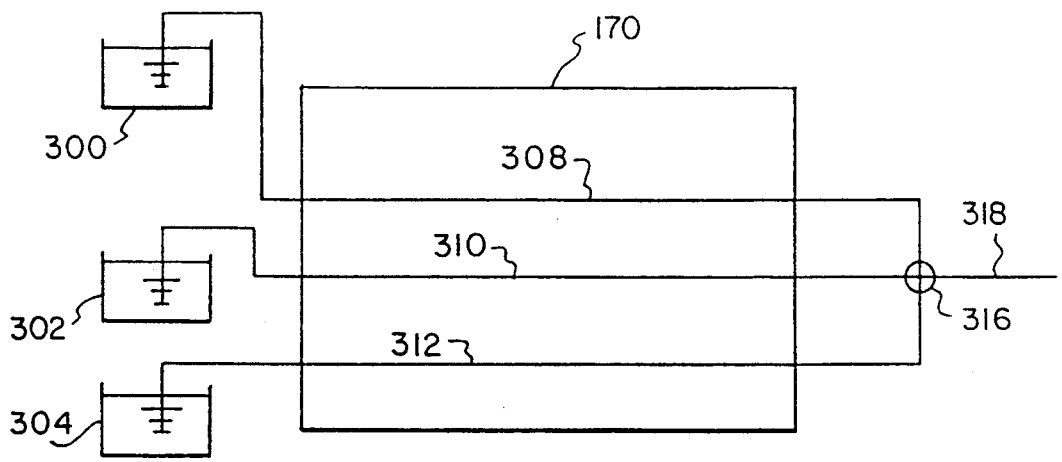
FIG. 3 shows a schematic diagram of a prior art degasser used to degas components of a mixed solvent.
Figure 4:
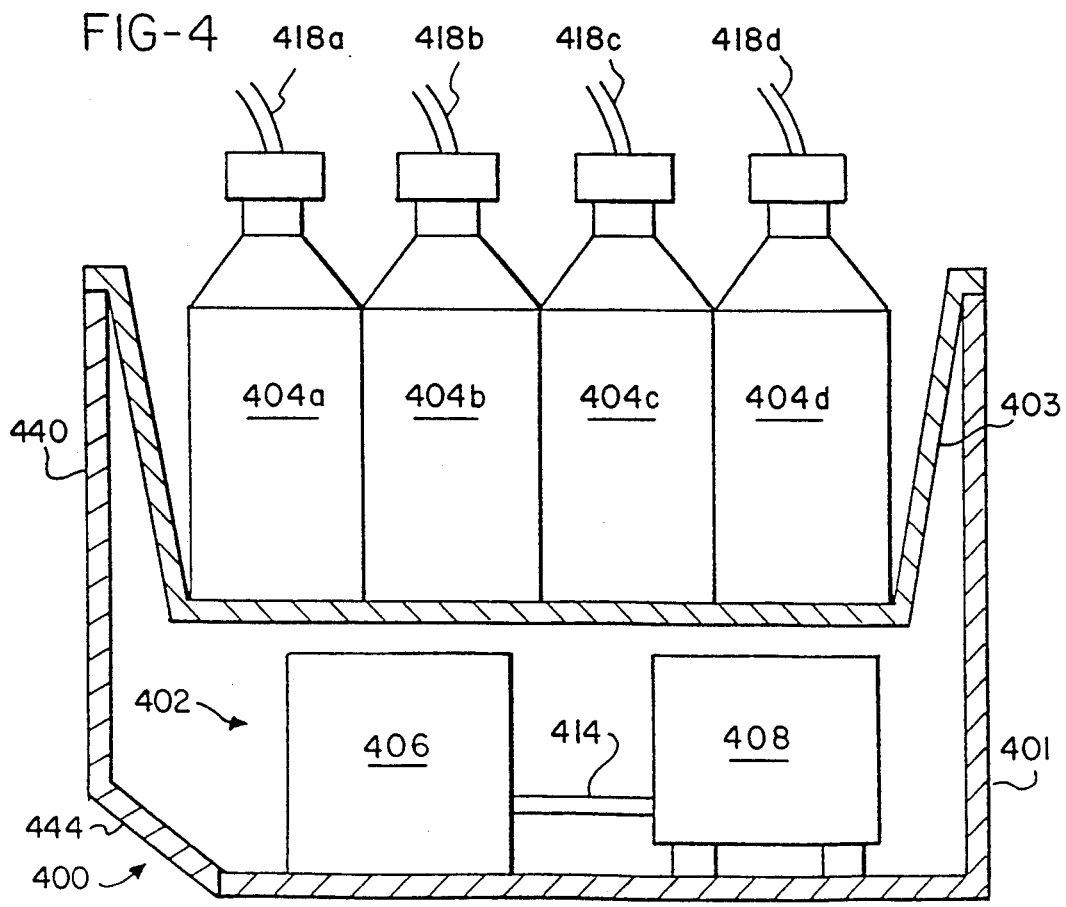
FIG. 4 shows a cross-section of a solvent conditioning module according to this invention.

FIG. 4 shows a cross-section of "Pumpmate TM" (trademark of Spectra-Physics, Inc., of San Jose, Calif.), a solvent conditioning module 400 made in accordance with the present invention for degassing a mobile phase solvent. Solvent conditioning module 400 comprises a housing 401, a vacuum degassing unit 402 and a holder 403 positioned on top of vacuum degassing unit 402. Holder 403 holds bottles 404*a–d* containing components of the solvent. (Bottles 404*a–d* are not part of solvent conditioning module 400). Holder 403 defines a partially enclosed volume which is large enough to contain bottles 404 and a spill whose volume is at least 1.1 times the volume of the contents of any one of bottles 404*a–d*. Thus, for example, in one variation, each bottle 404*a–d* is a 1-liter bottle, and holder 403 is large enough to contain a 1.1-liter spill in addition to bottles 404*a–d*. However, holder 403 provides physical stability to bottles 404a–d making them less likely to slide off or tip over. Holder 403 is made of an essentially inert material. Further, holder 403 can be lifted and removed from housing 401 for easy cleaning. A door 440 is provided in housing 401 for access to vacuum degassing unit 402. Door 440 is snapped in place, and can be opened by applying upward pressure to a slanted door portion 444. In use, degassing unit 402 is preferably sealed within housing 401 so that a liquid spill from bottles 404a–d does not enter degassing unit 402 and its circuitry.

Vacuum degassing unit 402 comprises a vacuum chamber 406 and a vacuum pump 408 which creates a vacuum in vacuum chamber 406 by pumping air out via a path 414. As further shown in FIG. 5, the solvent components are conducted from their respective bottles 404a–d via the respective tubing 418a–d to vacuum chamber 406.

Figure 5:
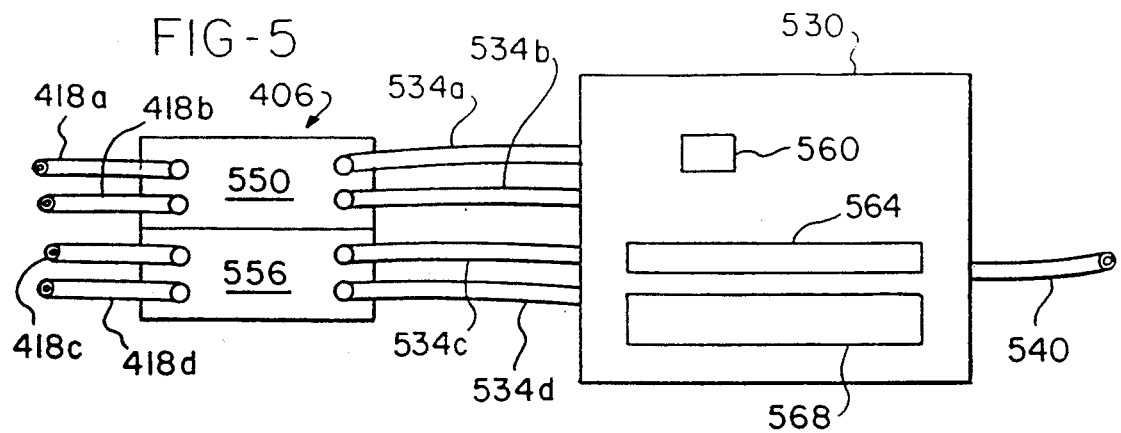
FIG. 5 shows schematically a side view of a vacuum chamber and a liquid chromatography pump according to this invention.

FIG. 5 further shows a liquid chromatography pump (LC pump) 530 which is outside solvent conditioning module 400. Referring to FIGS. 4 and 5, LC pump 530 pumps the solvent component from bottle 404a through tubing 418a to vacuum chamber 406 where the solvent component is degassed, and then through tubing 534a into LC pump 530 itself. Likewise, LC pump 530 pumps solvent components from each bottle 404b, 404c, 404d through respective tubing 418b, 418c, 418d to vacuum chamber 406, and then through respective tubing 534b, 534c, 534d into LC pump 530 itself. Tubing 418 (e.g. 418a–418d) is laced to a wall of housing 401 so that tubing 418 cannot be easily snagged. Tubing 534 (e.g. 534a–534d) passes through an opening (not shown) between door 440 and a wall of housing 401. The solvent components from different bottles 404 are mixed inside pump 530 in precise proportions by means of standard solvent proportioning techniques such as described in *SP8800/8810 LC Pump Operators Manual* (Spectra-Physics, 1987, Part Number A0099-235 9/88 D) available from Spectra-Physics of San Jose, Calif. and hereby incorporated by reference herein. LC pump 530 then pumps the mixed solvent through tubing 540 to an LC analytical system (not shown in FIGS. 4 and 5). Tubing 418, tubing 534, and tubing 540 are typically made of Teflon (a registered trademark of the DuPont Corporation).

Referring to FIG. 5, in one embodiment shown, vacuum chamber 406 is constructed of two vacuum cartridges: top cartridge 550 for degassing the solvent components from bottles 404a and 404b, and bottom carriage 556 for degassing the solvent components from bottles 404c and 404d. The interiors of cartridges 550 and 556 communicate so that both cartridges 550 and 556 are at vacuum at the same time.

LC pump 530 includes for control purposes a software-programmed microprocessor 560, a keyboard 564 and a display 568 to allow the user to monitor the level of the solvent components in bottles 404. When the solvent components are placed in respective bottles 404, the user enters the initial level of each solvent component on keyboard 564. As LC pump 530 pumps the solvent, microprocessor 560 calculates the amount of each solvent component pumped out from bottles 404 and the levels of the solvent components remaining in bottles 404 are continuously updated and displayed on display 568. When solvent conditioning module 400 is about to run out of at least one solvent component, LC pump 530 generates a signal to alarm the human operator.

In one embodiment of LC pump 530, a weight sensor sensing the weight of bottles 404 is used to determine the initial level of each solvent component in each bottle 404. In another embodiment of LC pump 530, a separate weight sensor is used for each bottle 404. The weight from each sensor is entered into LC pump 530 automatically.

Further variations in the use and structure of the solvent conditioning module 400 and LC pump 530 of the present invention shown in FIGS. 4 and 5 are possible. For example, solvent conditioning module 400 can be used to condition solvents having less than four components (including solvents having only one component). Correspondingly, in such cases less than four bottles 404 are used, or different bottles 404 are filled by the same component. Other variations of solvent conditioning module 400 can accommodate more than four bottles 404 in holder 403 while still other variations can accommodate only one, two or three bottles 404.

Further, in some variations, the solvent component from each bottle 404 is pumped through vacuum chamber 406 by a separate LC pump 530, and the solvent components are mixed at the outputs of the respective LC pumps.

In yet some other variations, the LC pump (or pumps) 530 is connected in the flow path of the solvent to tubing 418 upstream of vacuum chamber 406. So positioned, the solvent (or solvent components) in LC pump 530 is in an undegassed state. One drawback of this variation is that gas bubbles in the solvent get hung up in check valves and pistons of LC pump 530 and disrupt the flow rate of LC pump 530. Thus, placing LC pump 530 downstream of vacuum chamber 406 is advantageous.

Figure 6:
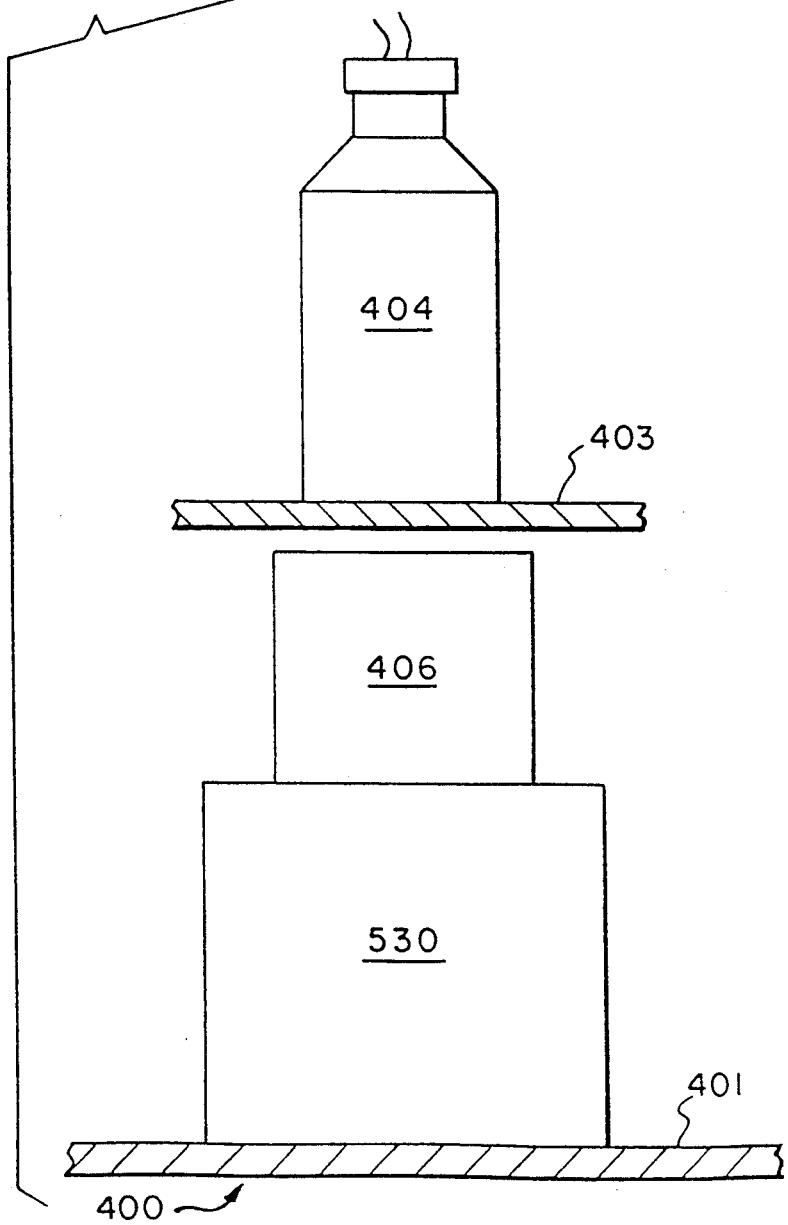
FIG. 6 shows a cross-section of another solvent conditioning module according to this invention.

Referring now to FIG. 6, a variation of solvent conditioning module 400 is shown in which LC pump 530 is placed under vacuum chamber 406. Such construction allows closer coupled tubing between vacuum chamber 406 and LC pump 530. Moreover, mounting the holder 403 with bottles 404 above vacuum degassing unit 402 provides head pressure into LC pump 530 and thus generally improves the solvent flow from bottles 404 to the LC analytical system.

Figure 7:
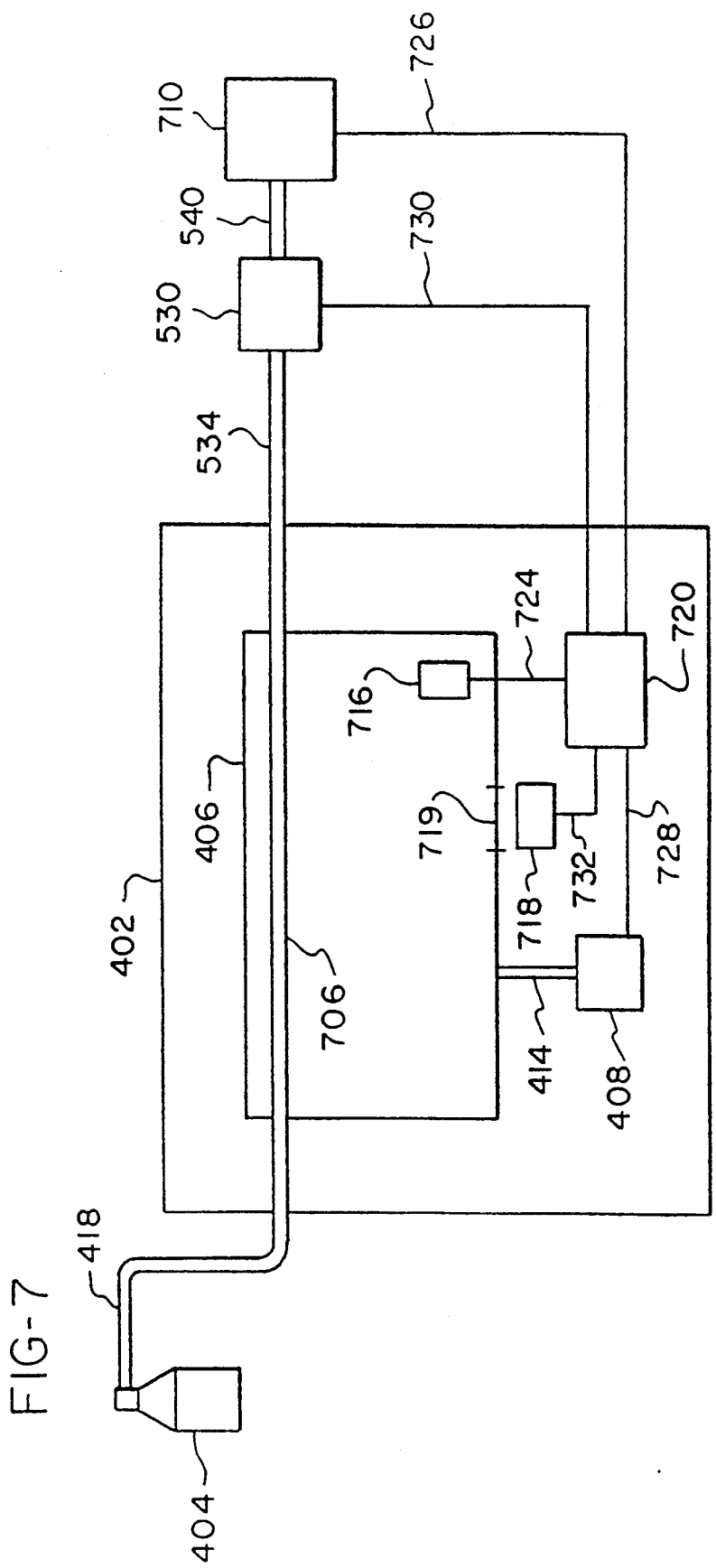
FIG. 7 shows a schematic diagram of a vacuum degassing unit according to this invention.

FIG. 7 shows a schematic diagram of the vacuum degassing unit 402 of solvent conditioning module 400. As before, the solvent (or solvent component) is conducted from bottle (or bottles) 404 by tubing 418 to vacuum chamber 406. Only one bottle 404 is shown for simplicity. Shown here in greater detail, the solvent is degassed in vacuum chamber 406 while in a solvent conduit 706. Solvent conduit 706 is gas permeable tubing. In an alternative embodiment, when vacuum degassing unit 402 degasses one solvent component, solvent conduit 706 is a membrane; the solvent component flows above the membrane, and a vacuum is created below the membrane. In either case, solvent conduit 706 is made of an essentially inert material permeable to gas, typically of Teflon. The walls of solvent conduit 706 are thinner than the walls of tubing 418. From vacuum degassing unit 402, the degassed solvent is conducted by tubing 534 to LC pump 530 and from there by tubing 540 to LC analytical system 710. Vacuum pump 408 creates a vacuum in vacuum chamber 406 by pumping air out via path 414. A vacuum sensor 716 senses the level of vacuum in vacuum chamber 406. A light radiator 718, typically an infra-red light bulb, radiates infra-red light toward solvent conduit 706 when it is desirable to heat the solvent and solvent conduit 706. Heating the solvent is sometimes advantageous in degassing because it may decrease the solubility of gas in the solvent. See Bakalyar, Bradley and Honganen, supra, hereby incorporated by reference herein, at page 280. Heating solvent conduit 706 is desirable because it increases the permeability of the Teflon walls of conduit 706 to gas. The light is transmitted through clear window 719 in the wall of vacuum chamber 406. Light radiator 718 transmits energy across the vacuum more efficiently that a conventional heat-radiating, i.e. radiant, heater because vacuum is not a good conductor of heat but is a good conductor of infra-red light.

In some variations, light radiator 718 is placed inside vacuum chamber 406. In some variations, light radiator 718 radiates other types of electromagnetic energy rather than infra-red light.

Still referring to FIG. 7, circuitry 720 receives signals from vacuum sensor 716 and LC analytical system 710 via respective signal paths 724 and 726 and controls vacuum pump 408, LC pump 530 and light radiator 718 via respective signal paths 728, 730 and 732. In particular, circuitry 720 provides indications to the operator when vacuum sensor 716 senses that a proper level of vacuum has been reached in vacuum chamber 406. Circuitry 720 receives, from LC analytical system 710 via signal path 726, data regarding chromatographic conditions in analytical system 710 and controls vacuum pump 408 and LC pump 530 so as to optimize the chromatographic conditions. For example, if the level of oxygen in the mobile phase solvent in analytical system 710 is too high, circuitry 720 slows down LC pump 530 so as to lower the flow rate of the solvent through vacuum chamber 406 allowing more oxygen to be extracted during degassing. In one variation, circuitry 720 detects an occurrence of a chromatographic run from the signals from LC analytical system 710 via signal path 726, and stops vacuum pump 408 for the duration of the run so as not to change the oxygen level in the solvent during the run. Changes in the oxygen level in the solvent during the run could lead to a baseline drift of a chromatographic detector (not shown). See Bakalyar, Bradley and Honganen, supra.

FIG. 8 is a schematic diagram of a portion of vacuum degassing unit 402, showing a variation thereof. In FIG. 8, a chamber 800 connects to tubing 418 which is located in the path of fluid flow between bottles 404 and vacuum chamber 406 upstream of vacuum chamber 406. A ceramic heating element 802 in chamber 800 is positioned in the flow path of the solvent (or solvent component) for contact with the solvent, and heats the solvent more efficiently than a heat-radiating heater in a vacuum chamber. The temperature level of heater 802 is controlled by circuitry 720 via signal path 804.

Alternatively, in the embodiment of FIG. 9, tubing 418 passes through a thermal chamber 920 maintained at atmospheric pressure, and positioned between bottles 404 and vacuum chamber 406. The air in thermal chamber 920 is heated by a heat-radiating heater 930. Tubing 418 transmits the heat to the solvent. A fan 940 circulates the air in thermal chamber 920 to transmit the heat to the solvent more efficiently. Circuitry 720 controls heater 930 and fan 940 via respective signal paths 950 and 960. The air in thermal chamber 920 conducts heat more efficiently than the remaining air molecules at vacuum in vacuum chamber 406. Thus, heating the solvent in thermal chamber 920 by heat-radiating heater 930 is more efficient than heating the solvent in vacuum chamber 406 by such a heater.

FIG. 10 is a schematic diagram of a portion of a degassing unit 402, showing another variation thereof which enhances the access of the solvent to the walls of the conduit 706. When vacuum chamber 406 is at vacuum, gas is extracted from the portions of the solvent close to the walls of solvent conduit 706. It may be desirable to agitate the solvent in conduit 706 so as to bring other portions of the solvent closer to the walls of conduit 706. In the variation of FIG. 10, an ultrasonic device 1010 emits ultrasound waves that impact the solvent in conduit 706 and thereby agitate the solvent. The ultrasonic energy of ultrasonic device 1010 is controlled by circuitry 720 via a signal path 1020.

Connector 1024 connecting vacuum pump 408 to conduit 706 provides another means for agitating the solvent. In this variation, vacuum pump 408 vibrates when operated. Connector 1024 transmits the vibrations of vacuum pump 408 to conduit 706. The vibrations agitate the solvent.

Figure 11:
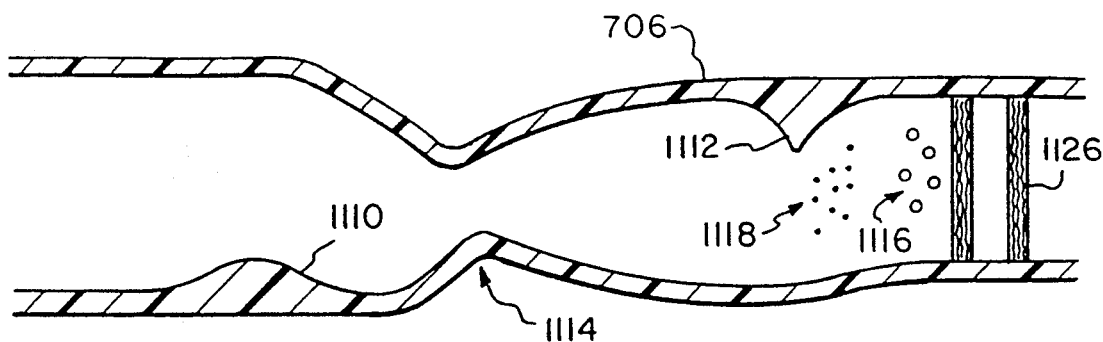
FIG. 11 shows a cross-section of a solvent conduit according to this invention.

FIG. 11 shows, in cross-section, one embodiment of solvent conduit 706 where means for agitating the solvent are illustratively included in conduit 706. Solvent conduit 706 is Teflon tubing. Its inner surface has an uneven portion so as to agitate the solvent as it flows by. Namely, the inner surface of conduit tubing 706 includes bumps such as bump 1110 and/or ridges such as ridge 1112. Conduit tubing 706 also may comprise a pinched portion 1114 to further agitate the solvent. Glass beads 1116 and magnetic particles 1118 may be provided inside conduit tubing 706 in order to further agitate the solvent. Magnetic particles 1118 are agitated by a conventional magnetic stirrer (not shown) located adjacent tubing 706. A portion of conduit tubing 706 downstream of glass beads 1116 and magnetic particles 1118 is packed by a column packing material 1126, the same material that is used to pack a chromatography column (not shown). In one variation, magnetic particles 1118 are held in place by an external magnetic field.

Figure 12:
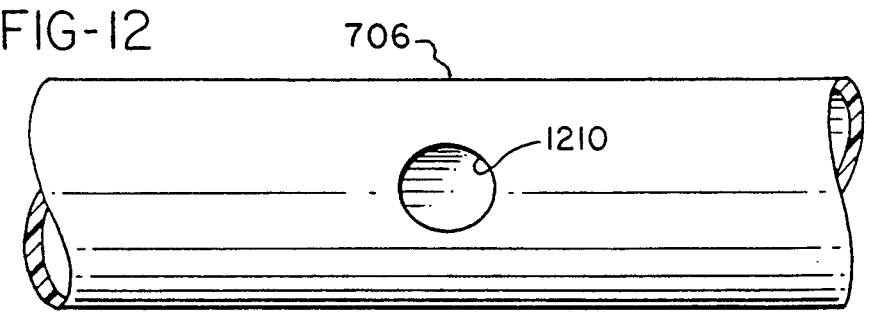
FIG. 12 shows a side view of another solvent conduit according to this invention.

In another embodiment of conduit tubing 706 shown in FIG. 12, conduit tubing 706 has an internal sealed off section (hole) 1210 to further agitate the solvent as it passes through. In general, conduit tubing 706 can be deformed in many ways to agitate the solvent.

Figure 13:
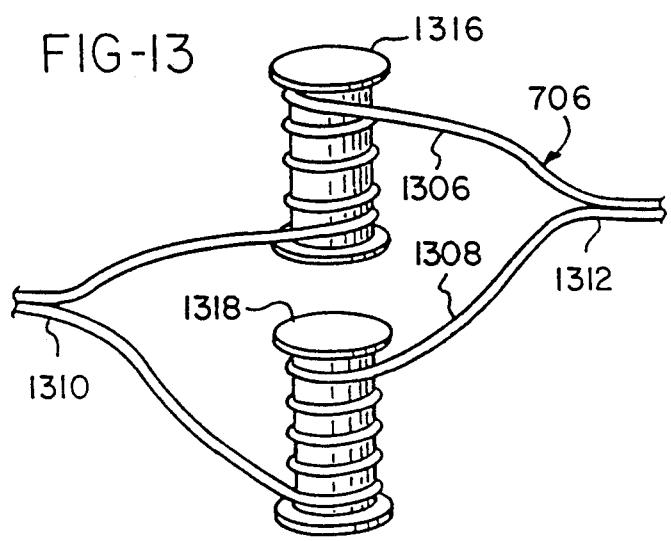
FIG. 13 shows schematically another solvent conduit according to this invention.

To further increase the amount of gas extracted from the solvent in a vacuum chamber, it is desirable to maximize the conduit tubing surface area exposed to vacuum. To that end, conduit tubing 706 of FIG. 13 is separated into two tubes 1306 and 1308 which interconnect portions 1310 and 1312 of conduit tubing 706. Tube 1306 is wound in coils around bobbin 1316, and tube 1308 is wound in coils around bobbin 1318. Bobbins 1316 and 1318 serve to separate the coils of tubes 1306 and 1308 so that the surfaces of the coils do not touch but are exposed to the surrounding vacuum. Namely, the adjacent coils of tube 1306 are spaced from each other, and the adjacent coils of tube 1308 are spaced from each other. Further, the coils of tube 1306 are spaced from the coils of tube 1308. In other variations, more than two tubes such as tube 1306 and tube 1308 are used, with each tube wound around its own bobbin.

Figure 14:
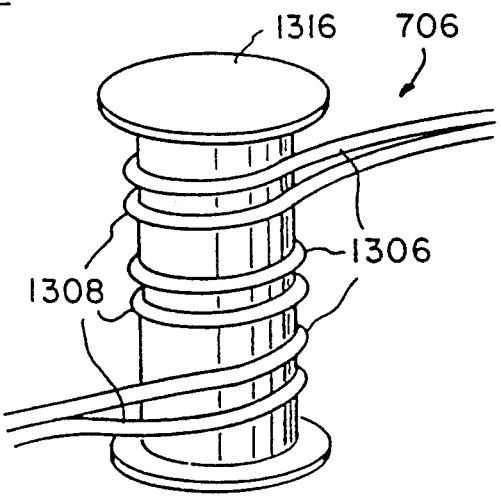
FIG. 14 shows schematically another solvent conduit according to this invention.

In the variation of FIG. 14, both tubes 1306 and 1308 are wound around the same bobbin 1316. The coils of tube 1306 alternate with the coils of tube 1308. In another variation, conduit 706 comprises only one tube wound in coils around a bobbin so that the adjacent coils of the tube are spaced from each other. In other variations, conduit 706 comprises more than two tubes separated into groups of one or more tubes each, the tubes of each group wound around a respective bobbin.

In some variations, conventional wire structures hold the coils of the tubes of conduit tubing 706 so as to separate the coils from each other.

To facilitate the use of multiple tubes and bobbins in the vacuum chamber, and increase conduit tubing surface area, the present invention further provides a multiple tube plug, and a method for connecting thin-walled tubes to a connector. As shown in the exploded view of FIG. 19, conduit 706 includes a multi-tube plug 760 and a plurality of small diameter, gas permeable tubes 1306 and 1308. Male plug 750 is provided at the terminus of tubing 418. More or less than the tubes 1306 and 1308 representatively shown can be connected to plug 760. As further shown in FIG. 20, a plurality of tubes, representatively shown as seven tubes, 1306, 1308, 1306a, 1308a, 1306b, 1308b, 1306c, can be connected to plug 760, and can be wound around bobbins singly or in groups, as described above. Each end of conduit 706 may be provided with plugs 760 to connect to tubing 418 and 534 via plugs 750.

Further, in accordance with the present invention, a method for connecting thin-walled tubes, such as tubes 1306, 1308 to a connector plug 760, is provided. The method makes possible the leak-tight connection of a plurality of small diameter, thin-walled tubes to a single plug. Such tubes are difficult to connect to plugs, and leakage at such connections has plagued the prior art. The method makes possible the insertion of a tube through a hole which is slightly smaller than the outside diameter of the tube. To accomplish this result, tubing made of Teflon ® or other material which has good chemical resistance and is gas permeable, is stretched. As the length of the tube is increased, the diameter decreases proportionally. This change in shape will last until the tubing is heated to above its gel temperature, when it will spring back to its original size.

More specifically, the method involves: stretching the tube; cutting the tube generally in the middle of the stretched area; threading the decreased diameter tube end through a hole in the plug block, the hole being slightly smaller than the original outside diameter of the tubing; pulling the tube end through the block until the unstretched tube is forced into the hole; and cutting off the tubing end which has been pulled through the hole, leaving a short section extending beyond the hole; and heating the exposed end of the tube.

Figure 19:
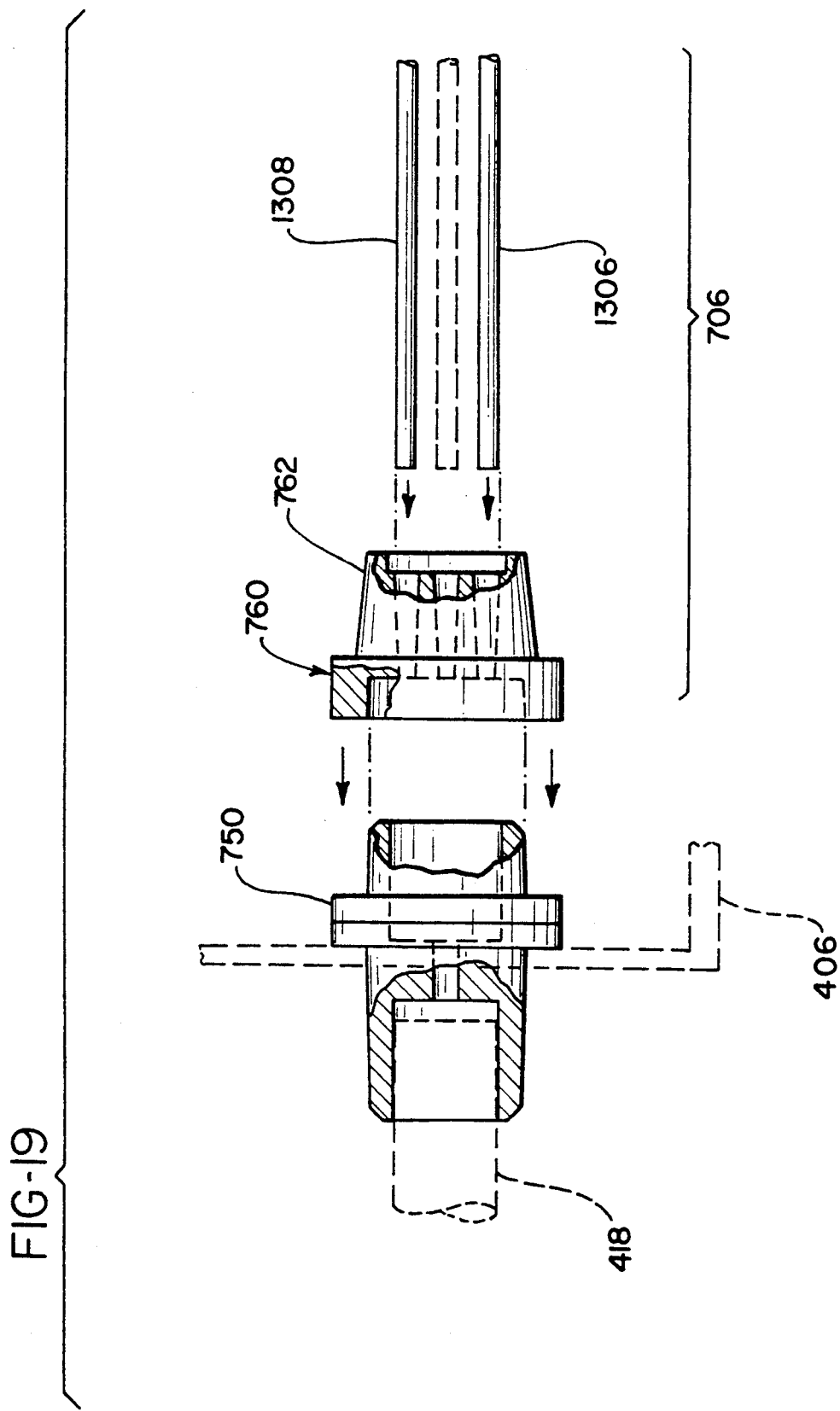
FIG. 19 shows an exploded view of the connector according to the present invention.

The step of threading the decreased diameter tube end is preferably performed in the direction indicated by the arrows in FIG. 19. The method, however, can be performed by threading in the other direction, but such is not preferred. The tapered holes in plug block 762 shown in FIG. 19 have a minimum hole diameter through which the tubes must be threaded. While tapered holes are preferred to facilitate molding of the plug block 762, the holes may also be straight through holes. Heating the tube will return the tube to its original shape. After heating, the exposed end of the tube will be larger than The hole and thus locked in place. Furthermore, if the tube had been flattened during the stretching and cutting steps, it will now be restored to its original round shape, leaving a clear flow path for fluids.

It is preferred to use tubing made of Teflon ®, made by DuPont de Nemours or a close relative thereto, for example Tefzel ®, also made by DuPont de Nemours. When such material is also used for the plug 760 and block 762, heating both the tube and the block 762 above the gel temperature will result in an actual bond or weld of the tube to the plug block 762. For example, for Teflon ®, depending on the exact kind, the gel temperature is approximately in the range of 600°-650° F. In addition, the tubes will return to their original shapes. If many tubes are connected to the same block 762, they can all be heated at the same time. In accordance with this method, a connector plug 760 having leak-tight connections to a plurality of thin-walled gas permeable tubes is simple to produce, and the labor for each plug 760 is not extensive. Use of the plug 760 permits increased surface to volume ratio for the fluid passing therethrough to enhance degassing.

Mixed mobile phase solvents are often used in liquid chromatography. In some cases, the solubility of certain gases in a mixed solvent is lower than the solubility of the gases in the components forming the solvent. It is then desirable to mix the components before degassing the solvent rather than to degas each component and then mix the degassed components. This degassing method is illustrated schematically in FIG. 15. Bottles 1510, 1512, 1514 each contain a separate component of a mobile phase solvent. The components flow through respective tubing 1520, 1522, and 1524 and mix in tubing 418 before entering vacuum chamber 406. The mixed solvent is degassed in vacuum chamber 406 and is then conducted to LC analytical system 710 (not shown in FIG. 15).

FIG. 16 shows schematically an autosampler 1610 that forms part of LC analytical system 710 (shown generally in FIG. 7). Autosampler 1610 includes a multiport valve 1614, syringe 1630, injector valve 1640, and several tubes. Referring to FIG. 16, when port 1612 of multiport valve 1614 is connected to port 1618, syringe 1630 is connected to a tube 1634 and, through a loop 1638 of an injector valve 1640, to a tube 1644 and a sample container 1648. A syringe plunger 1650 is withdrawn by a predetermined distance so that a precisely metered amount of the sample is drawn from sample container 1648 through tube 1644 into loop 1638. Injector valve 1640 is then rotated to inject the sample in loop 1638 into the mobile phase, arriving via tubing 540. See *SP8780/8775 Autosampler Operators Manual* (Spectra-Physics, 1987, Part Number A0099-263 8/87 A) available from Spectra Physics of San Jose, Calif. and hereby incorporated herein by reference. The mobile phase carries the sample via tubing 1651 to a chromatography column (not shown) for separation and analysis.

Sample container 1648 is then removed and replaced by a waste container (not shown). Syringe plunger 1650 is pushed in to expel the remaining syringe contents through tube 1634 and tube 1644 into the waste container. Autosampler 1610 is then flushed using the flush solvent in bottle 1660a. Namely, multiport valve 1614 is rotated so as to connect port 1612 to port 1670. Bottle 1660a is connected to port 1670 via tube 1674a, vacuum degassing unit 1676, and tube 1680a. A solvent conduit (not shown) similar to conduit 706 of FIG. 7 passes through vacuum degassing unit 1676 and connects tube 1674a to tube 1680a. The solvent conduit already contains a certain amount of degassed flush solvent from bottle 1660a. Syringe plunger 1650 is withdrawn to pull a suitable volume of the degassed flush solvent by syringe 1630. Multiport valve 1614 is rotated so as to connect port 1612 to port 1618. Syringe plunger 1650 is pushed in so as to expel the flush solvent into the waste container. This procedure of pulling in the flush solvent by syringe 1630 and expelling the flush solvent into the waste container is repeated until syringe 1630, tubes 1634 and 1644, and injector valve 1640 are considered flushed clean of any residual sample. Vacuum degassing unit 1676 in some embodiments is one of the vacuum degassing units described above with reference to FIGS. 4–15.

The flush solvent is degassed because gas in the flush solvent can adversely affect the performance of LC analytical system 710. Bubbles of gas can form in the flush solvent or the sample and cause inaccuracies in the amount of the sample drawn in by syringe 1630. When the sample amount is in the range of several microliters to several hundred microliters, the inaccuracies can be significant.

In some embodiments, syringe 1630 is replaced by some other means for pumping the flush solvent. In some embodiments, the same vacuum degassing unit 1676 is used to degas the mobile phase solvent and the flush solvent. That is, vacuum degassing unit 402 of FIG. 7 and vacuum degassing unit 1676 are one and the same vacuum degassing unit.

Figure 17:
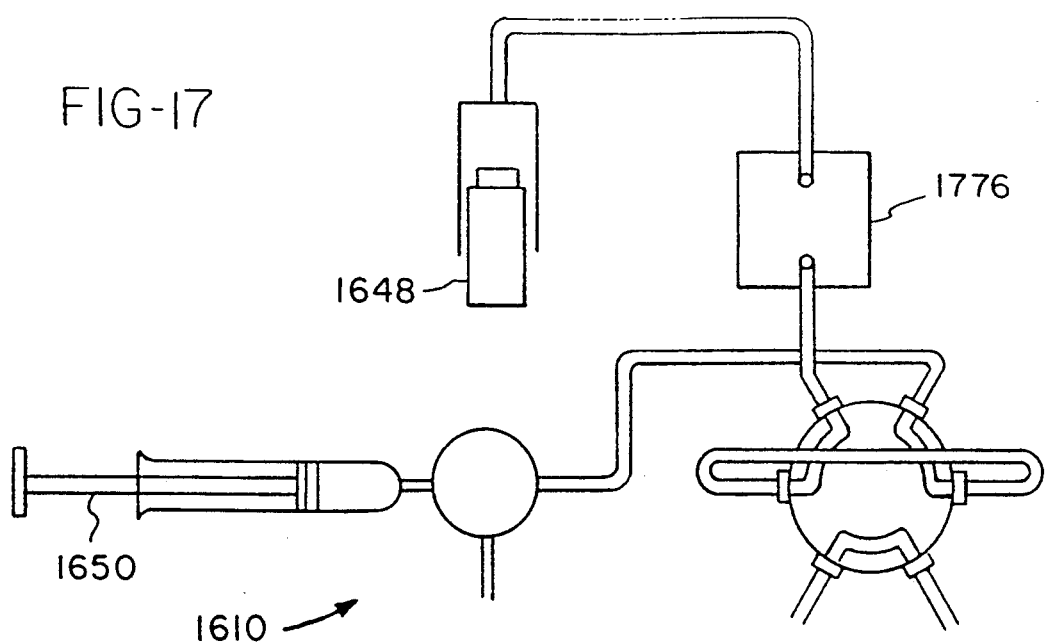
FIG. 17 shows a schematic diagram of another autosampler according to this invention.

FIG. 17 shows a portion of a variation of autosampler 1610 in which a vacuum degassing unit 1776 is used to degas the sample. The degassed sample is injected into the mobile phase or, alternatively, returned to the same or another sample container 1648 (by pushing syringe plunger 1650 in) for further processing. Vacuum degassing unit 1776 is used in some embodiments to degas flush solvents and the mobile phase.

Autosampler 1610 of FIGS. 16 and 17 is used also to dilute the sample in sample container 1648 by diluents and reagents. (A reagent is a solution that reacts with the sample.) Referring to FIG. 16, bottles 1660a, 1660b, and 1660c containing solvents or solutions that act as diluents and/or reagents are connected to respective ports 1670, 1690, and 1692 of multiport valve 1614 via respective tubes 1674a, 1674b and 1674c, via vacuum degassing unit 1676 and via respective tubes 1680a, 1680b and 1680c as shown in FIG. 16. Multiport valve 1614 is turned to connect port 1612 to port 1670, and syringe plunger 1650 is withdrawn by a predetermined distance to draw a predetermined amount of the solvent from bottle 1660a by syringe 1630. Multiport valve 1614 is then turned to connect port 1612 to port 1690, and syringe plunger 1650 is withdrawn further by a predetermined distance to draw a predetermined amount of the solvent from bottle 1660b by syringe 1630. Similarly, a predetermined amount of the solvent from bottle 1660c is drawn by a syringe 1630. Multiport valve 1614 is then turned to connect port 1612 to port 1618, syringe plunger 1650 is pushed in, and the solvent mixture is delivered to sample container 1648. The sample diluted by the solvent mixture is then analyzed using liquid chromatography or other analytical methods.

In some applications, each solvent or solution is delivered to sample container 1648 separately. The solution from bottle 1660a is drawn by syringe 1630 and expelled into sample container 1648. Then the solution from bottle 1660b is drawn by syringe 1630 and expelled into sample container 1648. Then the solution from bottle 1660c is draw in and expelled. In another variation, the solution from bottle 1660a is delivered to sample container 1648 separately, and the solutions from bottles 1660b and 1660c are drawn in one after another and then expelled together. Other variations are possible.

In some variations, more or less than three solutions are used. Multiport valve 1614 is replaced by a combination of valves in some embodiments.

In some embodiments, the same vacuum degassing unit 1676 is used to degas the diluents and the reagents, flush solvents, mobile phase solvents and the sample. In one variation, bottle 1660a contains a flush solvent, and bottles 1660b and 1660c contain diluent and reagent solvents. In some embodiments, several vacuum degassing units are used, each vacuum degassing unit for degassing one or more diluents, reagents, flush solvents and the mobile phase.

To summarize, autosampler 1610 is combined with one or more vacuum degassing units for sample preparation for chemical analysis and for sample injection where high precision in the sample preparation and injection is required. Additional tubing and plumbing is used as necessary to connect bottles and other containers with the sample and the solvents to the vacuum degassing units.

Figure 18:
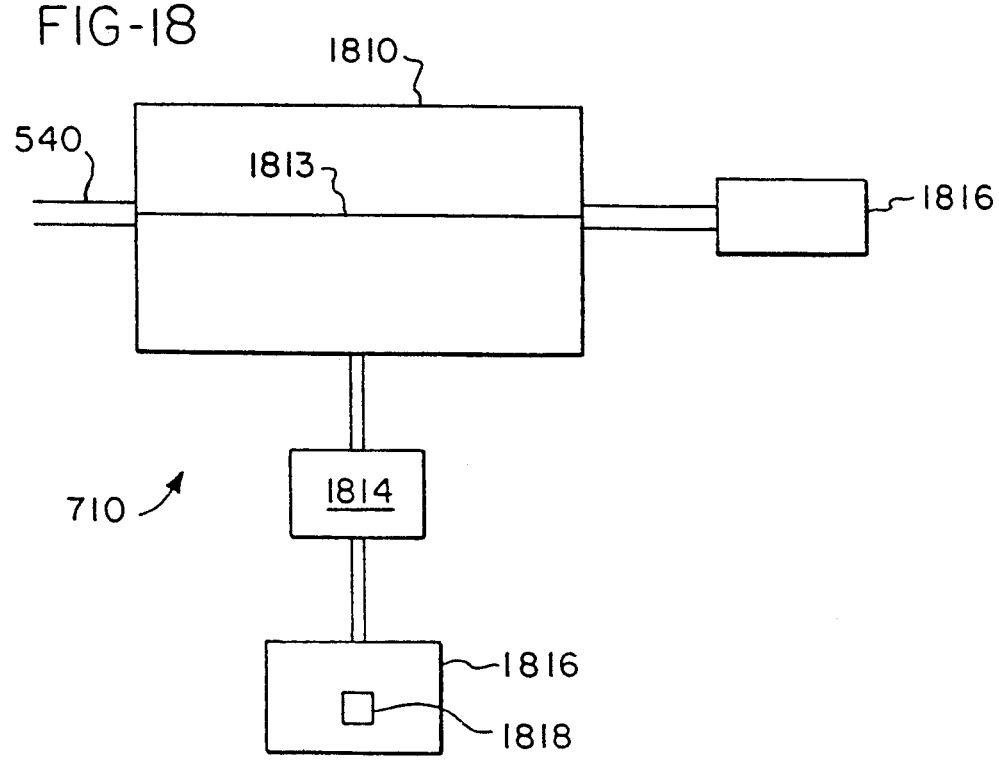
FIG. 18 shows a schematic diagram of a portion of a liquid chromatography analytical system according to this invention.

Gases dissolved in the sample being analyzed carry chromatographic information about the sample. Liquid chromatography analytical system 710 of FIG. 18 has its own vacuum chamber 1810 for extracting gas from the sample. The sample arrives via tubing 540, is degassed in vacuum chamber 1810 while in conduit 1813, and is conducted to column 1816 for further analysis. Vacuum pump 1814 creates vacuum in vacuum chamber 1810 and conducts the gas extracted from the sample to chamber 1816 where the gas is condensed. Gas sensor 1818 in chamber 1816 senses the gas and produces chromatographic information from the gas.

Turning now to further aspects of the present invention, it has been found that the walls of solvent conduit 706 of FIG. 7 become contaminated with time by particles suspended in the solvents. Such contamination decreases the effectiveness of degassing. Thus, it is desirable to provide the user with a method for testing solvent conduit 706 so that the user can clean or replace the contaminated conduit. Conduit 706 is tested in accordance with the present invention as follows. Referring to FIG. 7, a gas is introduced into conduit 706 instead of a solvent. Vacuum pump 408 is operated until a predetermined level of vacuum is reached in vacuum chamber 406. Vacuum pump 408 is then turned off. The gas leaks out of conduit 706, and the vacuum level decays. The time of decay is measured, and the condition of conduit 706 is determined from the time of decay. The longer the time, the more contaminated is the conduit 706. The time of decay can be compared to standards or to decay time measured during initial operation of the vacuum degassing unit 402.

Sometimes it is desirable in liquid chromatography to use a mobile phase having certain gases dissolved in it. Vacuum degassing unit 402 of FIG. 7 is also used to provide such a mobile phase. When the mobile phase (or a component thereof) is in solvent conduit 706, the gas is supplied under pressure into vacuum chamber 406 by vacuum pump 408. A portion of the gas permeates the walls of solvent conduit 706 and dissolves in the mobile phase. The mobile phase is then conducted to LC analytical system 710.

While certain representative embodiments and details have been shown for purposes of illustrating the invention, it will be apparent to those skilled in the art that various changes in the apparatuses and methods disclosed herein may be made without departing from the scope of the invention, which is defined in the appended claims.

What is claimed is:

1. A method for providing a mixed mobile phase to a liquid chromatography analytical system, comprising the steps of:
   providing at least two components of a mobile phase, mixing the components of said mobile phase and obtaining the mixed mobile phase;
   placing said mixed mobile phase into a chamber;
   creating a vacuum in said chamber so as to degas said mixed mobile phase; and
   conducting the degassed mixed mobile phase to said analytical system.

2. A module for conditioning a liquid, comprising:
   means for degassing said liquid;
   a container having said liquid therein;
   means for conducting said liquid from said container to said degassing means comprising tubing connected to said container and a pump; and
   a holder mounted on top of said degassing means, for holding said container and liquid to provide stability thereto and to contain any liquid which may spill from said container.

3. The module of claim 2, wherein said container comprises one or more bottles for holding said liquid, and wherein said holder is adapted to contain a spill from any one of said one or more bottles.

4. The module of claim 2, wherein said degassing means is mounted on top of said pump.

5. An autosampler comprising:
   means for injecting a sample into a mobile phase;
   a vacuum degassing unit for degassing a solvent and obtaining a degassed solvent, said unit comprising a vacuum chamber including a vacuum pump for creating a vacuum in said vacuum chamber, tubing for conducting said solvent through said chamber, said tubing being permeable to gases in said solvent; and
   means for conducting said degassed solvent through said injecting means.

6. The autosampler of claim 5, wherein said injecting means comprises:
   an injector valve;
   means for pumping a controllable amount of liquid; and
   a first valve having a first port connected to said pumping means and a second port connected to said injector valve; and
   wherein said conducting means comprises:
   means for connecting said vacuum degassing unit to a third port of said first valve and said pumping means.

7. An autosampler comprising:
   an injector valve;
   first means for connecting said injector valve to a sample container having a liquid sample therein;
   means for pumping a controllable amount of liquid from said sample container;
   a first valve having a first port connected to said pumping means;
   second means for connecting said first valve to said injector valve and to said sample container;
   means for vacuum degassing a plurality of solvents, said vacuum degassing means comprising a vacuum chamber including a vacuum pump for creating a vacuum in said vacuum chamber, tubing for conducting said solvents through said chamber, said tubing being permeable to gases in said solvents; and
   means for conducting each degassed solvent of said plurality to said first valve.

8. The autosampler of claim 7, wherein said second means comprises means for connecting a second port of said first valve to said injector valve;
   wherein said conducting means comprises means for conducting each of said degassed solvents to a unique one of a plurality of ports of said first valve; and
   wherein said first valve is operative to selectively connect said first port to any single one of said second port and said ports of said plurality of ports.

9. An autosampler comprising:
   an injector valve;
   a vacuum degassing unit;
   means for connecting a sample container to said vacuum degassing unit; and
   means for connecting said vacuum degassing unit to said injector valve.

* * * * *